United States Patent
Sienkiewicz

(10) Patent No.: US 8,532,354 B2
(45) Date of Patent: Sep. 10, 2013

(54) METHOD FOR PROVIDING VISUAL SIMULATION OF TEETH WHITENING

(76) Inventor: Alexander Sienkiewicz, Palo Alto, CA (US)

( * ) Notice: Subject to any disclaimer, the term of this patent is extended or adjusted under 35 U.S.C. 154(b) by 136 days.

(21) Appl. No.: 13/305,595

(22) Filed: Nov. 28, 2011

(65) Prior Publication Data
US 2012/0134558 A1 May 31, 2012

Related U.S. Application Data

(60) Provisional application No. 61/417,507, filed on Nov. 29, 2010.

(51) Int. Cl.
- G06K 9/00 (2006.01)
- G06K 9/46 (2006.01)
- G06K 9/66 (2006.01)
- G06K 9/40 (2006.01)
- G06K 9/20 (2006.01)
- G06K 9/36 (2006.01)

(52) U.S. Cl.
USPC ........... 382/128; 382/282; 382/283; 382/274; 382/194

(58) Field of Classification Search
None
See application file for complete search history.

(56) References Cited

U.S. PATENT DOCUMENTS

| | | | |
|---|---|---|---|
| 7,912,265 B2 * | 3/2011 | Kemp et al. | 382/128 |
| 8,005,298 B2 * | 8/2011 | Sagawa | 382/167 |
| 2003/0198384 A1 * | 10/2003 | Vrhel | 382/190 |
| 2009/0092297 A1 * | 4/2009 | Kitoh et al. | 382/128 |

* cited by examiner

Primary Examiner — Stephen R Koziol
Assistant Examiner — Timothy Choi
(74) Attorney, Agent, or Firm — White-Welker & Welker, LLC; Matthew T. Welker, Esq.

(57) ABSTRACT

Method for enabling a teeth whitening simulator that is designed to help a user understand how the color of their teeth affects the look of their smile. The method executed by a computer, a mobile electronic device, an application on a smart phone, or equivalent machine. Selecting a Profile or uploading a photo or image. Detecting and determining the number and location of faces in a photo or image and the faces' associated teeth. Whitening is performed on the selected teeth and face. After whitening, a feathering feature may be used to more accurately simulate a more realistic image where the desired whitening level is blended around the borders of the teeth to the surrounding facial elements to provide a more natural looking simulation. Finally, to see how different shades of whitening might affect their image, a movable slider is provided to see the smile with different whitening values.

12 Claims, 4 Drawing Sheets

METHOD FOR PROVIDING VISUAL SIMULATION OF TEETH WHITENING

CROSS REFERENCE TO RELATED APPLICATIONS

This application claims priority from U.S. Provisional Patent Application Ser. No. 61/417,507, entitled "A method for providing visual simulation of teeth whitening", filed on 29 Nov. 2010.

FEDERALLY SPONSORED RESEARCH

Not Applicable

SEQUENCE LISTING OR PROGRAM

Not Applicable

TECHNICAL FIELD OF THE INVENTION

The present invention relates generally to a method for dental and other professionals to provide patients with information about and visual simulation of teeth whitening. More specifically, the present invention relates to method, embodied on computer software executable by a machine, for providing information about and visual simulation of teeth whitening.

BACKGROUND OF THE INVENTION

In recent years, teeth whitening has become a huge phenomenon. A whiter, brighter smile is one of the first things that people notice about your appearance. It's no mystery that whiter teeth make us look better: younger, more attractive, and more confident. This is why men and women of all ages are now opting for teeth whitening systems to improve their smile.

Although whitening is very popular, many people are still clueless about the wide array of different products and procedures that are now available. Today, there are hundreds of products that all claim to give you whiter teeth in a very short time. But results can range from impressive to disappointing, or even non-existent.

With so many different kinds of systems and products to choose from, people have a difficult time selecting the right one, and having a realistic expectation of the results. It is therefore an objective of the present invention to teach a teeth whitening simulator that is designed to help a user understand how the color of their teeth affects the aesthetics of their smile.

SUMMARY OF THE INVENTION

One of the biggest concerns during teeth bleaching is how white one should go. It is difficult to objectively look at ones' self in the mirror and decide what their ideal level of whiteness should be. A person doesn't want their teeth too yellow, and they don't want their teeth too white. Generally speaking, women can pull off a whiter shade while males look better with a color that isn't a bleach white shade. Gender, Age, Skin Tone, and Hair Color are all factors you should take into consideration.

The objective of the present invention is to provide methods for enabling a teeth whitening simulator that is designed to help a user understand how the color of their teeth affects the look of their smile. In one embodiment, where the method is enabled by a website, a user may first select a Profile that best matches their features from the Menu, and the teeth whitening simulator will automatically find the face that best matches them or they can upload a photo or image directly to the website. In another embodiment, where the method is enabled by a smart phone or other mobile electronic device, a user typically uploads a photo or image for use by the whitening simulator.

Next the method, executed either by a website, an application on a smart phone or an application on any other electronic device such as a computer or electronic mobile device detects and determines the number and location of teeth in a profile or uploaded photo or image. Then whitening is performed on the selected teeth and face. After whitening, a feathering feature may be used to more accurately simulate a more realistic image where the desired whitening level is blended around the borders of the teeth to the surrounding facial elements to provide a more natural looking simulation. Finally, to see how different shades of whitening might affect the aesthetics of their face and smile, a user moves a slider to see the smile with different whitening values.

Before embarking on any whitening treatment, it is advantageous to the user/consumer to simulate their desired level of whiteness. This way a dentist or whitening professional can recommend a product that will achieve that result such as over the counter products, in-office products, or custom bleaching trays.

BRIEF DESCRIPTION OF THE DRAWINGS

The accompanying drawings, which are incorporated herein form a part of the specification, illustrate the present invention and, together with the description, further serve to explain the principles of the invention and to enable a person skilled in the pertinent art to make and use the invention.

DETAILED DESCRIPTION OF THE INVENTION

In the following detailed description of the invention of exemplary embodiments of the invention, reference is made to the accompanying drawings (where like numbers represent like elements), which form a part hereof, and in which is shown by way of illustration specific exemplary embodiments in which the invention may be practiced. These embodiments are described in sufficient detail to enable those skilled in the art to practice the invention, but other embodiments may be utilized and logical, mechanical, electrical, and other changes may be made without departing from the scope of the present invention. The following detailed description is, therefore, not to be taken in a limiting sense, and the scope of the present invention is defined only by the appended claims.

In the following description, numerous specific details are set forth to provide a thorough understanding of the invention. However, it is understood that the invention may be practiced without these specific details. In other instances, well-known structures and techniques known to one of ordinary skill in the art have not been shown in detail in order not to obscure the invention. Referring to the figures, it is possible to see the various major elements constituting the apparatus of the present invention.

Now referring to the Figures, the embodiment of the system and method for providing visual simulation of teeth whitening is illustrated. The method of the present invention is embodied by a software program containing executable instruction of the method and/or process claimed by the present invention. The software program embodying the present invention is executable on a particular machine or apparatus. "Particular machine" or "apparatus" is defined as a desktop computer, laptop computer, personal data assistance (PDA), IPAD, tablets, table computers, IPHONE, mobile phone, smart phone, or any other equivalent electronic device which is capable of running a set of executable instructions embodied by software and providing a display of the result of those instructions. These electronic devices used to define a particular machine or apparatus function tie the method of the present invention to a particular machine or apparatus.

Figure 1:
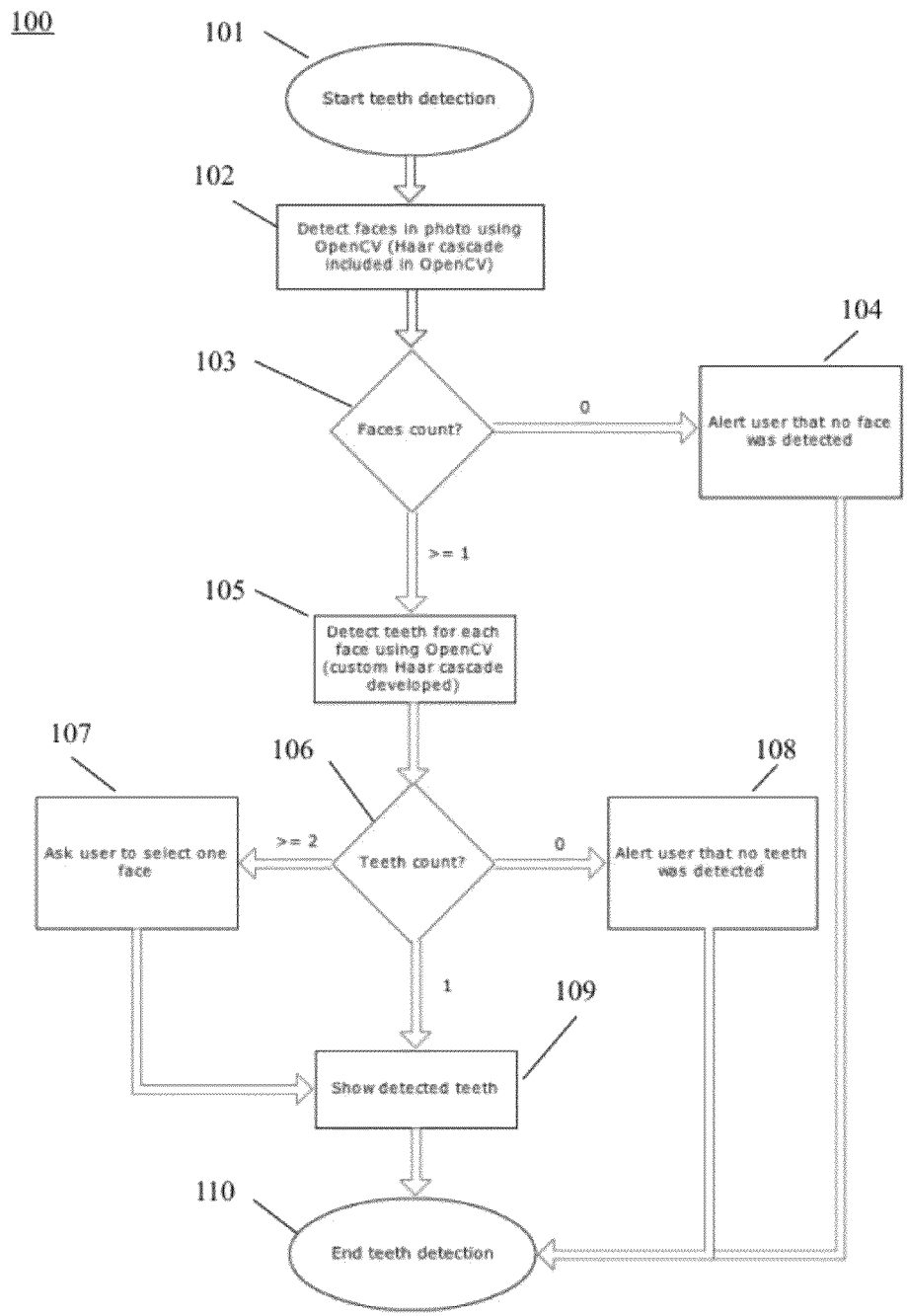
FIG. 1 is a flow chart illustrating the teeth detection method of the present invention.

Now referring to FIG. 1, the first step in the method is to determine, recognize, and locate the faces in an image from a profile image or an uploaded user image or photo and detect the teeth 101. The second step in the teeth detection process 100 is the detection of faces 102. The method uses Open CV with Haar cascade to detect faces and associate and detected teeth with each face in a photo or other image in step 102. OpenCV (Open Source Computer Vision) is a library of programming functions for real time computer vision. OpenCV is released under a BSD license; it is free for both academic and commercial use.

Figure 2:
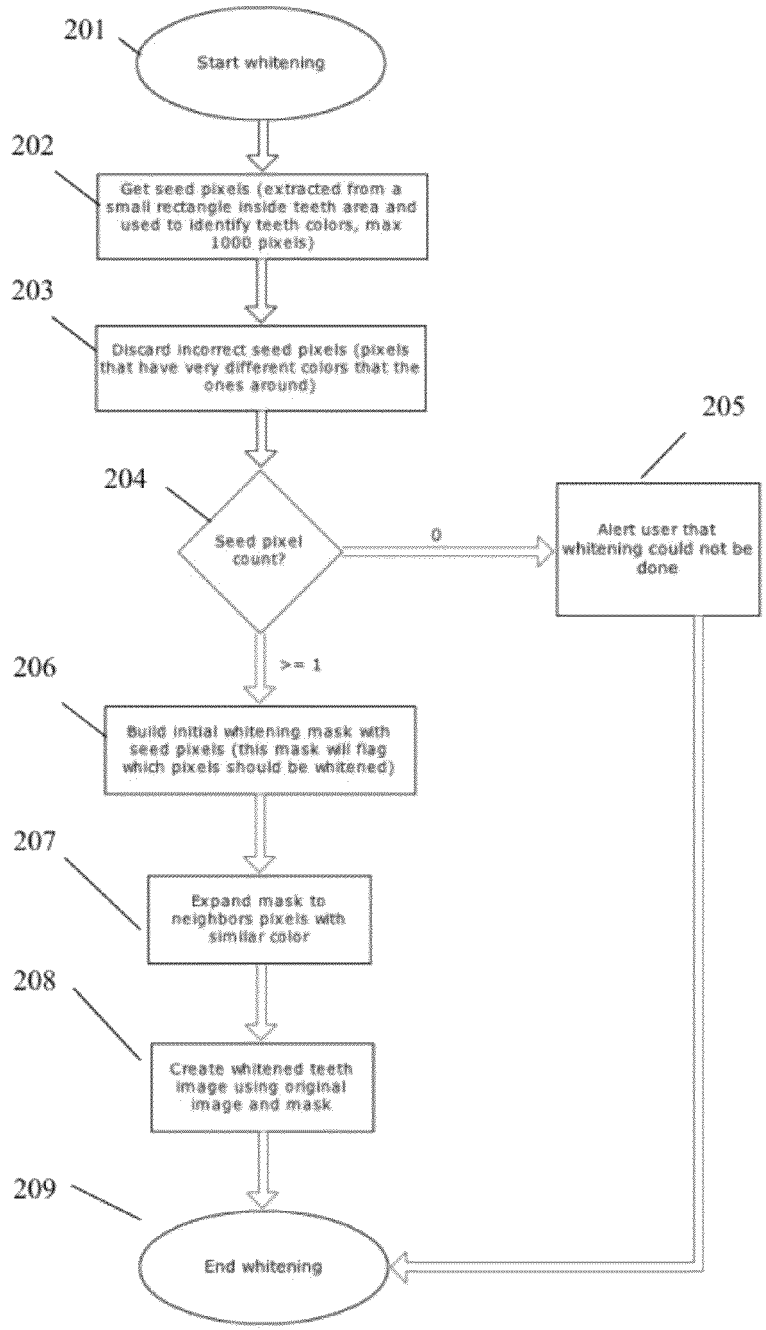
FIG. 2 is a flow chart illustrating the whitening method of the present invention.
Figure 3:
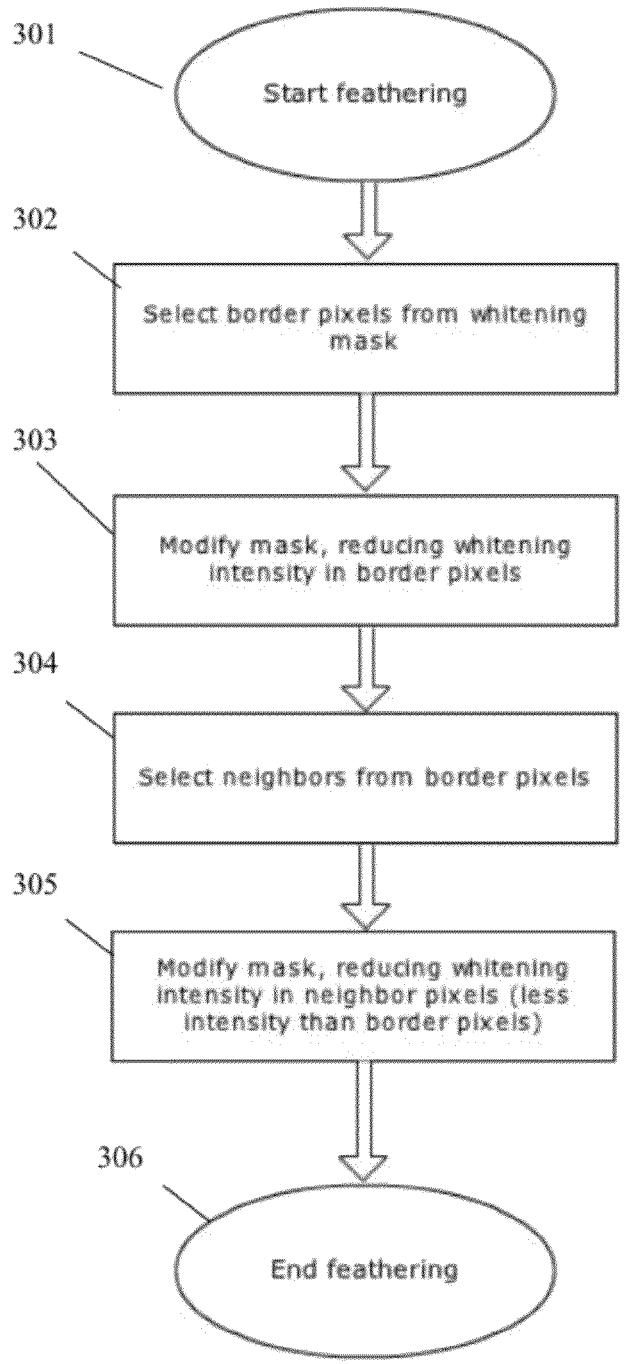
FIG. 3 is a flow chart illustrating the feathering method of the present invention.

The next step in the teeth detection process 100 occurs where a count is taken of the faces to determine the total number of faces in the photo or other image 103. If no faces are detected the teeth detection process ends 110 after alerting the user that no faces were detected 104. If one or more faces are detected the system then proceeds to detect the teeth associated with each face using OpenCV using a custom Haar cascade 105. A teeth count is then made to determine the number of faces associated with teeth 106. If there are no teeth, an alert is provided to a user notifying them that there are no teeth in the image 108 and the process ends 110. If the teeth count is one, the system automatically detects the face and its associated teeth 109, the detection process ends 110, and the whitening process 200 begins. If the teeth count is two or more, the user is notified and prompted to select from the two or more faces associated with the teeth count 107. A face selection is made in step 107 the selected face's associated teeth 109, the detection process ends 110, and the whitening process 200 begins Now referring to FIG. 2, after the teeth detection process 100 is complete, the teeth whitening process 200 begins after the face and corresponding teeth selection is made in step 109 of the teeth detection process 100. The whitening process begins 201 with the extraction of seed pixels from a small rectangle inside the teeth area that is used to identify the teeth colors 202. Currently, the max is 1000 pixels. The next step is to discard any incorrect seed pixels, which are those pixels that have very different colors from those around or adjacent to the pixel when a pixel is compared to the pixels around or adjacent to it 203. This is determined by comparing the difference between each pixel's RGB values. Then a formula is used to determine a difference value between neighboring pixels. If the difference value is below a predetermined threshold, the pixels are considered similar, if the difference value is above a predetermined threshold, the pixels are considered different or incorrect seed pixels.

Next the seed pixel count is then determined 204. If there are no seed pixels after the discarding step 203, an alert is sent to a user that whitening could not be done 205 and the whitening process ends 209. If the seed pixel count is one or more, the process continues and an initial whitening mask is built using the seed pixels 206. This mask will flag which pixels should be whitened. Next, an expanded mask to neighboring pixels with similar colors is created 207. The combination of the initial whitening mask and the expanded mask creates a whitened teeth image using the original image 208 and the whitening process ends 209.

Feathering may be used to enhance the appearance of the altered image. The feathering process 300 starts 301 by identifying and selecting border pixels 302 from the whitening mask created during the whitening process 200 illustrated in FIG. 2. This new, modified mask reduces whitening intensity in the border pixels 303. Neighboring pixels with respect to the border pixels are selected from the bordering pixels to create the modified mask 304. The modified mask reduces whitening intensity in neighbor pixels so that they have less intensity than border pixels 305 and the feathering process 300 ends 306. The feathering process 300 reduces the sharp contrast between the whitened or enhanced teeth in the photo or image along the border between the teeth and the surrounding skin, lips, gums, etc depending on the exposure of the teeth in the photo or image.

Figure 4:
FIG. 4 is an illustrative screen shot of a smart phone application using the methods of the present invention to create the visual simulation on a smart phone.

A teeth whitening simulator using the teeth detection 100, whitening 200, and feathering 300 methods of the present invention was designed to help a user better understand how the color of their teeth affects the look of their smile. The methods of the present invention allow a user to visually see how different shades of whitening might affect their image. In an exemplary simulator using the methods, a user would just move a slider 401 to see their smile visually displayed on a screen 400 in different whitening values as shown in FIG. 4.

Where shaded values are shown to a user, the shade values are derived from the VITAPAN SHADE GUIDE. This is a universally accepted guide, systematically arranged from light to dark, which all dentists refer to when communicating shade color. It has been used in dentistry for over 40 years. Most recently, the makers of this guide (VITAPAN) have come out with a 3D guide, but very few dentists have adopted it thus far. The values 010-040 are generally only attainable through bleaching.

Thus, it is appreciated that the optimum dimensional relationships for the parts of the invention, to include variation in size, materials, shape, form, function, and manner of operation, assembly and use, are deemed readily apparent and obvious to one of ordinary skill in the art, and all equivalent relationships to those illustrated in the drawings and described in the above description are intended to be encompassed by the present invention.

Furthermore, other areas of art may benefit from this method and adjustments to the design are anticipated. Thus, the scope of the invention should be determined by the appended claims and their legal equivalents, rather than by the examples given.

The embodiments of the invention in which an exclusive property or privilege is claimed are defined as follows:

1. A method for providing visual simulation of teeth whitening executable by a machine and rendered on the display of the machine, comprising the steps of:
   a teeth detection process comprising the steps of:
      detecting, determining, recognizing, and locating one or more faces in a photo or image;
      taking a count of the faces to determine the total number of faces in the photo or image;

determining, recognizing, and locating the teeth in an image;
associating the teeth with a face in an image;
selecting a face and associated teeth; and
a whitening process comprising the steps of:
extracting seed pixels from a small rectangle inside the teeth area that is used to identify the teeth colors;
discarding any incorrect seed pixels, which are those that have very different colors when compared to the ones around it;
determining the seed pixel count;
building an initial whitening mask using the seed pixels;
flagging which pixels should be whitened;
creating an expanded mask to neighboring pixels with similar colors;
combining the initial whitening mask and the expanded mask; and
creating a whitened teeth image using the original image with the combined initial whitening mask and the expanded mask.

2. The method of claim 1, wherein if no faces are detected the teeth detection process ends.

3. The method of claim 1, wherein Open CV with Haar cascade is used to detect faces in a photo or other image.

4. The method of claim 1, wherein
a teeth count is made to determine the number of faces associated with teeth; and
if one or more faces are detected the system then proceeds to detect and associate the teeth with a face.

5. The method of claim 2, wherein
a teeth count is made to determine the number of faces associated with teeth; and
if one or more faces are detected the system then proceeds to detect and associate the teeth with a face using OpenCV using a custom Haar cascade.

6. The method of claim 1, wherein
if there are no teeth, and alert is provided to a user notifying them that there are no teeth in the image;
if the teeth count is one, the system automatically detects the teeth and face and the detection process ends and the process continues with the whitening process; or
if the teeth count is two or more, the user is notified and prompted to select from the two or more faces associated with the teeth count.

7. The method of claim 1, wherein the step discarding any incorrect seed pixels is further comprise of the steps:
comparing the difference between each pixel's RGB values;
using a formula to determine a difference value between neighboring pixels;
if the difference value is below a predetermined threshold, the pixels are considered similar; and
if the difference value is above a predetermined threshold, the pixels are considered different or incorrect seed pixels.

8. The method of claim 1, wherein the step determining the seed pixel count is further comprise of the step:
if there are no seed pixels after the discarding step, an alert is sent to a user that whitening could not be done and the whitening process ends.

9. The method of claim 1, further comprising a feathering process comprising the steps of:
identifying and selecting border pixels from the whitening mask created during the whitening process;
reducing whitening intensity in the border pixels;
selecting neighboring pixels with respect to the border pixel;
creating a modified mask from the neighboring pixels and border pixels;
reducing whitening intensity in neighbor pixels in the modified mask so that they have less intensity than border pixels; and
reducing the sharp contrast between the whitened or enhanced teeth in the photo or image along the border between the teeth and the surrounding facial surfaces.

10. The method of claim 1, further comprising the steps of,
displaying a whitened teeth image on the screen or display of an electronic device; and
providing controls to change the whitening level displayed in the whitened teeth image.

11. The method of claim 1, wherein the control is a slider to display the whitened teeth image with different whitening shade values.

12. The method of claim 1, wherein shade values are derived from a universally accepted teeth shade color guide.

* * * * *